(12) United States Patent
Mann et al.

(10) Patent No.: US 6,315,928 B1
(45) Date of Patent: *Nov. 13, 2001

(54) SPIROFLUORENOPYRANS

(75) Inventors: Claudia Mann, Munich; Manfred Melzig, Wessling; Udo Weigand, Munich, all of (DE)

(73) Assignee: Optische Werke G. Rodenstock, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/786,206

(22) PCT Filed: Jun. 30, 2000

(86) PCT No.: PCT/EP00/06156

§ 371 Date: Mar. 2, 2001

§ 102(e) Date: Mar. 2, 2001

(87) PCT Pub. No.: WO01/02384

PCT Pub. Date: Jan. 11, 2001

(30) Foreign Application Priority Data

Jul. 2, 1999 (DE) .............................. 199 30 290

(51) Int. Cl.$^7$ ...................... C07D 311/96; C07D 493/10; C07D 495/10; G02B 5/23; C08K 5/15

(52) U.S. Cl. ............................ 252/586; 546/17; 546/269; 549/12; 549/330; 549/336; 549/337; 549/382; 252/586; 544/106

(58) Field of Search ........................... 544/106; 252/586; 549/336, 337, 382, 12; 546/269, 17

(56) References Cited

U.S. PATENT DOCUMENTS 5,645,767    7/1997    Van Gemert .
5,869,658    2/1999    Lin et al. .

FOREIGN PATENT DOCUMENTS

WO 96/14596    5/1996    (WO) .

*Primary Examiner*—Deborah C. Lambkin
*Assistant Examiner*—Andrea D'Souza
(74) *Attorney, Agent, or Firm*—Crowell & Moring LLP

(57) ABSTRACT

The present invention relates to specific photochromic 3H-naphtho[2,1-b]pyran derivatives and to their use in plastics of all types, especially for ophthalmic purposes. In particular, the present invention relates to spiro compounds derived from naphthopyrans and having a fluorene structure, referred to as spirofluorenopyrans, in which an annelated ring system is joined by a spiro bond to the central carbon atom of the fluorene structure.

7 Claims, No Drawings

SPIROFLUORENOPYRANS

This application is a 371 of PCT/EP00/06156 Jun. 3, 2000.

The present invention relates to specific photochromic 3H-Naphtho[2,1-b]-pyran derivatives and their use in plastics of all types, especially for ophthalmic purposes. In particular, the present invention relates to spiro compounds with a fluorene structure derived from naphthopyrans, called spirofluorenopyrans, in which an annelated ring system is joined by a spiro bond to the central carbon atom of the fluorene structure.

Various dye classes are known that change their color reversibly upon radiation with light of specific wavelengths, especially sunlight. Therefore, this means that these dye molecules transform into an excited, colored state due to the supply of energy in the form of light, which they leave again when the energy supply is interrupted, which means they return to their colorless, or at least hardly colored, normal state. These photochromic dyes include e.g., the naphthopyrans with various substituents that have already been described in the state of the art.

Pyrans, especially naphthopyrans and larger ring systems derived from them, are photochromic compounds that are still the object of intensive studies today. Although they were first submitted for a patent in the year 1966 (U.S. Pat. No. 3,567,605), it was not until the 1990's that compounds could be developed that seemed to be suitable for use in eyeglasses.

3H-Naphthopyrans derived from 2-naphthols, and their higher analog derivatives derived from them through annelation, are a group of photochromic dyes whose longest wavelength absorption maximum of the excited form lies predominantly in the spectral range from 420 nm to 500 nm and thus provide a yellow, orange or red color effect.

In this process, the bleaching rate is influenced by steric resistance or by electronic effects. The substituents of the aryl radicals on the carbon atom that is adjacent to the pyran oxygen atom are of primary importance. The steric influence of substituents in ortho-position of such aryl radicals is described, e.g., in U.S. Pat. No. 5,066,818. The electronic influence of substituents on these aryl rings or on the naphthalene radical itself affects both the absorption maximum and the bleaching rate. This is described e.g., in U.S. Pat. No. 5,520,853 and U.S. Pat. No. 5,623,005 as well as in WO 99/31082.

The 3H naphthopyrans derived from 2-naphthols known in the state of the art, and their higher analog derivatives derived by annelation are associated with disadvantages that, when used in sunglass lenses, significantly impair the wearing comfort of the person wearing the glasses. For one thing, the dyes known in the prior art frequently do not have a sufficient long wavelength absorption in the excited, as well as in the unexcited state. This also leads to problems in combinations with other photochromic dyes. In addition, there is also frequently too high of a temperature sensitivity with respect to the darkening, which at the same time means that bleaching occurs too slowly. Furthermore, the dyes described have an insufficient service life, as a result of which sunglasses of this type have an inadequate stability. The latter becomes noticeable from rapidly declining performance and/or a great deal of yellowing.

It is thus the object of the invention to provide new photochromic 3H-anphthopyrans that have improved properties in comparison to the compounds described in the state of the art. The photochromic compounds will be distinguished relative to similar compounds from the state of the art, in particular by faster kinetics in the excited form, i.e., a faster bleaching rate, and by better performance in durability testing. This object is achieved by the subjects identified in the claims. In particular, photochromic 3H-naphtho-[2,1-b]pyrans with the general formula (I) are provided:

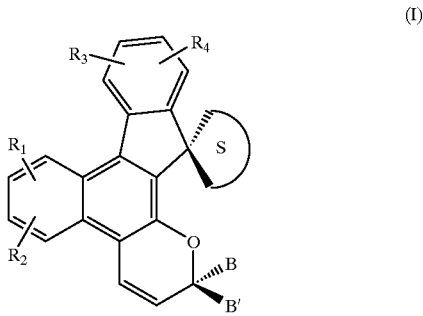

(I)

wherein the radicals $R_1$, $R_2$, $R_3$ and $R_4$ each independently represent a substituent selected from the group A, consisting of a hydrogen atom, a $(C_1-C_6)$-alkyl radical, a $(C_1-C_6)$-alkoxy radical, a $(C_3-C_7)$-cycloalkyl radical, which may contain one or more heteroatoms, a phenyl radical, a hydroxy group, bromine, chlorine and fluorine; the structural unit S together with the central spiro carbon atom, represents a saturated and/or unsaturated ring element with 5 to 8 carbon atoms, of which a maximum of one can be replaced by a heteroatom selected from the group consisting of O, S and $NR_5$, wherein the radical $R_5$ is a straight-chain or branched-chain $(C_1-C_5)$-alkyl radical, a substituted or unsubstituted $(C_5-C_7)$-cycloalkyl radical, a substituted or unsubstituted phenyl radical or a substituted or unsubstituted benzyl radical, wherein at least one aromatic or heteroaromatic ring system is annelated to the ring element, wherein the ring system is selected from the group E, consisting of benzene, naphthalene, phenanthrene, pyridine, quinoline, furan, thiophene, pyrrole, benzofuran, benzothiophene, indole and carbazole, and the ring system can have one or more substituents from the group A; B and B', independently of each other, are selected from one of the following groups a), b), c) or d), wherein a) includes monosubstituted, disubstituted and trisubstitutierted aryl radicals, wherein the aryl radical is phenyl or naphthyl;

b) includes unsubstituted, monosubstituted and disubstituted heteroaryl radicals, wherein the heteroaryl radical is pyridyl, furanyl, benzofuran-2-yl, benzofuran-3-yl, thienyl, benzothiene-2-yl or benzothiene-3-yl;

wherein the substituents of the aryl or heteroaryl radicals in a) and b) are selected from the group consisting of hydroxy, amino, mono-$(C_1-C_6)$-alkylamino, di-$(C_1-C_6)$-alkylamino, monophenyl and diphenylamino which are unsubstituted or monosubsituted in the aromatic rings, piperidinyl, morpholinyl, carbazolyl, unsubstituted, monosubstituted and disubstituted pyrryl, $(C_1-C_6)$-alkyl, $(C_1-C_6)$-alkoxy, bromine, chlorine and fluorine, wherein said aromatic and heteroaromatic ring systems can be substituted with $(C_1-C_6)$-alkyl, $(C_1-C_6)$-alkoxy, bromine, chlorine and fluorine;

c) includes structural units with the following formulas (V) and (W):

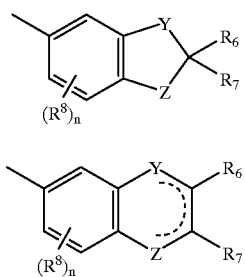

(V)

(W)

wherein
  Y and Z are independently O, S, CH, CH$_2$ or NR$_9$, wherein the R$_9$ radical is selected from the group D, consisting of (C$_1$–C$_6$)-alkyl, (C$_1$–C$_6$)-acyl and hydrogen, the radicals R$_6$ and R$_7$ independently represent hydrogen and/or a (C$_1$–C$_6$)-alkyl radical, and the radical R$_8$ is a substituent from the group A, wherein n is 1, 2 or 3, with the proviso that if Y in formula (V) is NR$_9$, Z is carbon, or
d) B and B' together form an unsubstituted, monosubstituted or disubstituted fluorene-9-xylene radical or a saturated hydrocarbon radical, which is C$_3$–C$_{12}$ spiromonocyclic, C$_7$–C$_{12}$ spirobicyclic and/or C$_7$–C$_{12}$ spirotricyclic, wherein the fluorene substituents are selected from the group A.

In a preferred embodiment, the structural unit S in the foregoing formula (I), together with the central spirocarbon atom, forms a substituted or unsubstituted fluorene, xanthene, thioxanthene or dihydroanthracene unit.

Preferred photochromic 3H-naphtho[2,1-b]pyrans have the following general formulas (II):

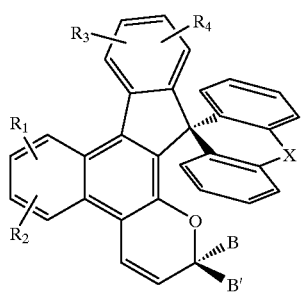

(II)

wherein R$_1$, R$_2$, R$_3$ and R$_4$ are defined as above, and X stands for —CH$_2$—, —O—, —S— or a C—C single bond between the phenyl rings.

In an especially preferred embodiment, B and B' in the formula (II) set forth above are independently monosubstituted, disubstituted and trisubstituted aryl radicals wherein the aryl radical is a phenyl radical or a naphthyl radical in each case.

Especially preferred compounds according to the invention include:
Spiro-9-fluoreno-13'-[6-methoxy-2-(4-methoxyphenyl)-2-phenyl-indeno[2,1-f]-naphtho[2,1-b]pyran],
Spiro-9-xantheno-13'-[6-methoxy-2-(4-methoxyphenyl)-2-phenyl-indeno[2,1-f]-naphtho[2,1-b]pyran],
Spiro-9-thioxantheno-13'-[6-methoxy-2-(4-methoxyphenyl)-2-phenyl-indeno[2,1-f]-naphtho[2,1-b]pyran],
Spiro-9-(9,10-dihydroanthraceno)-13'-[6-methoxy-2-(4-methoxyphenyl)-2-phenyl-indeno[2,1-f]naphtho[2,1-b]pyran] and
Spiro-9-fluoreno-13'-[6,7-dimethoxy-2-(4-methoxyphenyl)-2-phenyl-indeno[2,1-f]-naphtho[2,1-b]pyran].

FIG. 1 shows a method of synthesis for producing exemplary photochromic compounds according to the invention.

In accordance with the present invention, compounds are produced by spirocyclic ring formation on the fluoreno structure of the naphthopyran skeleton, which distinguish themselves from the compounds known in the prior art both by a better aging behavior as well as by a faster bleaching from the darkened state.

EP-A-0 987 260 actually describes the positive influence that a bridging in indeno-annelated naphthopyran derivatives, which are derived from the 1-naphthol system, has on service life. If this bridging is applied to the annelated ring systems derived from 2-naphthols, as described in U.S. Pat. No. 5,869,658, a definite improvement of the service life can be expected here as well. However, in contrast to the compounds in EP-A 0 987 260, no influence is expected on the bleaching rate of the compounds according to the invention, since no steric influence results here during the ring closure of the pyran ring. Although the compounds according to the invention are clearly more sterically substituted in comparison to the compounds described in U.S. Pat. No. 5,869,658, surprisingly their bleaching rate is much faster compared to the compounds described in U.S. Pat. No. 5,869,658. In this process, it is particularly notable that when the structural unit S in general formula (I) is a fluorene, xanthene, thioxanthene or dihydroanthracene unit, the bleaching rate can be modified by almost a factor of 3 by a slight mutual spreading of the two phenyl rings of the structural units mentioned above by the substituents X in the general formula (II). The linking to spiro systems in accordance with the invention thus leads not only to an improvement in service life, but also simultaneously presents a simple option for influencing the bleaching rate without simultaneously having to change the absorption maximum due to electronic effects.

The compounds according to the invention can be used in plastic materials and/or plastic objects of any type and form for a number of application purposes for which photochromic behavior is important. In this process, one dye according to the present invention or a mixture of such dyes can be used. For example, the photochromic naphthopyran dyes according to the present invention, can be used in lenses, especially ophthalmic lenses, glass for eyeglasses of all types, e.g., ski glasses, sunglasses, motorcycle glasses, visors of protective helmets, and the like. In addition the naphthopyrans according to the invention can also be used e.g., for sun protection in vehicles and living rooms in the form of windows, protective shutters, covers, roofs, etc.

To manufacture such photochromic objects, the photochromic naphthopyran dyes according to the invention can be applied to or embedded in a polymer material, such as an organic synthetic resin material, by various processes described in the prior art, as already indicated in WO 99/15518.

In this process, a distinction is made between mass coloring and surface coloring methods, as they are called. A mass coloring method comprises, e.g., the dissolving or dispersion of the photochromic compound or compounds according to the present invention in a plastic material, e.g., by addition of the photochromic compound(s) to a monomer material before polymerization occurs. Another option for manufacturing a photochromic object is permeation of the plastic material or materials with the photochromic compound(s) by immersing the plastic material in a hot solution of the photochromic dye(s) according to the present invention or e.g., by a thermal transfer method. The photochromic compound(s) can also be provided e.g., in the form of a separate layer between adjacent layers of the plastic material, e.g., as a part of a polymer film. In addition, application of the photochromic compound(s) as a part of the coating found in the surface of the plastic material is also possible. In this process, the term "permeation" will mean the migration of the photochromic compound(s) into the plastic material, e.g., by a solvent-supported transfer of the photochromic compound(s) into a polymer matrix, vapor phase transfer or other surface diffusion processes of this type. In an advantageous manner, such photochromic objects, e.g., eyeglasses, are made not only using the usual mass coloring, but in the same manner also by means of surface coloring, whereby in the latter variation a surprisingly low tendency to migrate can be achieved. This is especially advantageous in subsequent manufacturing steps since layer separations and similar defects can be drastically reduced, e.g., with an antireflective coating, by lower reverse diffusion in a vacuum.

All in all, based on the photochromic 3H-naphtho[2,1-b]pyrans according to the invention, any desired compatible (compatible with regard to chemistry and type and manner of coloration) coloring agents, i.e., dyes, can be applied on the plastic material or embedded in it, in order to satisfy esthetic considerations as well as medical or fashion aspects. As a result, the dye(s) which are specifically selected can vary depending on the intended effects and requirements.

The photochromic 3H-naphtho[2,1-b]pyrans according to the invention with the general formula (I) or (II) can be produced, e.g., according to the reaction scheme shown in FIG. 1.

The synthesis method of the spiro compounds according to the invention has been considerably modified in comparison to the method described in U.S. Pat. No. 5,869,658. While in synthesis according to U.S. Pat. No. 5,869,658 (see also the comparison compound listed in Table 1), the fluorenone intermediate product (reaction product from step iv) of the reaction diagram shown in FIG. 1) has to be obtained by oxidation of the corresponding fluorene, in the context of the present invention it is produced directly during cyclization. Starting with benzylcyanide derivatives, the corresponding 2-acetyl compounds are produced according to step i) by ester condensation with ethyl acetate. After hydrolysis and decarboxylation, the corresponding phenyl acetone derivatives (step ii) are produced. The double ester condensation with phthalic acid dimethylester (step iii) produces 2-phenylacetylindane dione derivatives, which in turn form the starting materials for intramolecular cyclization to the desired hydroxyfluorenone derivatives according to step iv). These are finally reacted with 2-propin-1-ol derivatives according to step v) to indeno-annelated naphthopyran derivatives. This step as well as the two subsequent steps take place analogously to the reactions with isomeric hydroxyfluorenone derivatives, as described in EP-A-0 987 260. In step vi), the reaction occurs with suitable Grignard reagents that can be cyclized in step vii) to the spirocompounds according to the invention; see FIG. 1.

In the following, as an example, the production of selected 3H-naphtho[2,1-b]pyrans according to the invention is described in detail, whereby these examples naturally do not restrict the scope of protection of the present invention, but are used only for purposes of illustration.

EXAMPLES

Example 1 i) A mixture of 3-methoxybenzylcyanide (100 g), acetic acid ethyl ester (90 g) and potassium ethylate (78 g) in 1000 ml of absolute toluene were heated to boiling for 4 hours with stirring and reflux. Then 600 ml of water was added, and the organic phase was separated in a separating funnel. This was extracted again with 600 ml of water. The concentrated aqueous phases were extracted twice with ether and then the aqueous phase was acidified with concentrated hydrochloric acid. Extraction was carried out twice with 400 ml portions of ether and the concentrated organic phase was washed with water and diluted sodium hydrogen carbonate solution. After drying over sodium sulfate and distilling off the solvent, a viscous oil was obtained (103 g) which solidified at room temperature and was identified by the NMR spectrum as 2-(3-methoxyphenyl)-3-oxo-butanoic acid nitrile.

ii) A mixture of 175 ml concentrate sulfuric acid and 50 ml water was cooled in an ice bath with stirring. After addition of the reaction product (100 g) obtained in step i), the mixture was heated briefly until it dissolved. Then it was cooled again in the ice bath and 900 ml water was added. The reaction mixture was heated to boiling 6 hours with stirring and reflux. After cooling, extraction with carried out twice with 400 ml portions of ether, and the concentrated organic phase was washed twice with water and diluted sodium hydrogen carbonate solution. After drying over sodium sulfate and distilling off the solvent, the raw product was subjected to column chromatography with aluminum oxide (water content 3%) as the stationary phase and dichloromethane as the mobile phase. The product was a yellowish oil (45 g) that was identified by NMR spectroscopy as 3-methoxyphenylacetone.

iii) A mixture of the reaction product obtained in step ii) (33 g), phthalic acid dimethylester (39 g) and sodium methylate (17 g) in 400 ml absolute toluene was heated to boiling for 4 hours with stirring and reflux (see Ind. Eng. Chem. 1942, P. 494). After addition of 300 ml of water, the mixture was stirred briefly. A precipitate developed (sodium enolate of the product) between the two phases. It was allowed to cool to room temperature and then the resulting solid separated by vacuum filtration and washed with ether and water. The solid was dissolved in 500 ml water at boiling temperature and acidified with concentrated hydrochloric acid. After cooling and stirring, the solid formed was separated by vacuum filtration and dried at 60° C. The light yellow product (22 g) was identified by NMR spectroscopy as 2-(3-methoxyphenylacetyl)-indane-1,3-dione.

iv) The reaction product obtained in step iii) (13 g) was suspended in 200 ml of phosphoric acid and placed in an oil bath preheated to 120° C. with stirring. After 1.5 hours at 120° C., an orange-colored suspension had formed. After cooling, the reaction mixture was poured into 800 ml of water with stirring, and the suspension was separated by vacuum filtration. The filter residue was washed thoroughly with water and dried at 60° C. The orange-colored product (12 g) was identified by NMR spectroscopy as 6-hydroxy-3-methoxy-7H-benzo[c]fluorene-7-one.

v) 3 g of the reaction product obtained in step iv) was suspended in about 300 ml of toluene together with 1-(4-methoxyphenyl)-1-phenyl-1-propinol (4 g; produced from 4-methoxybenzophenon and sodium acetylide in DMSO). After addition of a spatula tip of 4-toluene sulfonic acid, the reaction mixture was heated to boiling 1.5 hours with stirring and reflux. After brief cooling, the toluene was removed under vacuum, and the residue was dissolved in 40 ml of dichloromethane and subjected to column chromatography with aluminum oxide (water content 3%) as the stationary phase and a dichloromethane/hexane mixture (2:1) as the mobile phase. The red product band was collected. After removal of the solvent, a dark red product (3 g) was obtained, which was identified by NMR spectroscopy as 2-(4-methoxyphenyl)-2-phenyl-6-methoxy-13-oxo-indeno[2,1-f]naphtho[2,1-b]pyran.

vi) 2 g of the reaction product obtained in step v) was dissolved in 50 ml of absolute THF with stirring. 2 equivalents of 2-biphenylyl magnesium bromide (produced from 2-bromobiphenyl and magnesium chips in THF solution) were dripped into this solution. The reaction mixture was stirred 1 hour at room temperature. Then the reaction mixture was poured into water, acidified with concentrated hydrochloric acid until the phases were clear, and the organic phase was separated. After extraction with water, drying over sodium sulfate and removal of the solvent, a brownish oil (2 g) was obtained which was identified by NMR spectroscopy as 13-(2-biphenylyl)-13-hydroxy-6-methoxy-2-(4-methoxyphenyl)-2-phenyl-indeno[2,1-f]naphtho[2,1-b]pyran.

vii) 1 g of the reaction product obtained in step vi) was cyclized under heating in 30 ml of glacial acetic acid. After the addition of one drop hydrochloric acid, heating to boiling was continued for 5 min, and hot water was added until the reaction solution became cloudy. After cooling, extraction was carried out with ether. The organic phase was washed with water and diluted sodium hydrogen carbonate solution. After drying over sodium sulfate, the solvent was distilled off, and the raw product was dissolved in 40 ml dichloromethane and subjected to column chromatography with aluminum oxide (water content 3%) as the stationary phase and a dichloromethane/hexane mixture (2:1) as the mobile phase. After distilling off the eluent from the product fraction, a solid (0.5 g) was obtained that was identified by NMR spectroscopy as spiro-9-fluoreno-13'-[6-methoxy-2-(4-methoxy-phenyl)-2-phenyl-indeno[2,1-f]naphtho[2,1-b]pyran].

Example 2

The procedure was analogous to example 1 with the exception that in step vi) the reaction was carried out with 2-phenoxyphenylmagnesium bromide (produced from 2-bromodiphenylether and magnesium in THF solution) instead of with 2-biphenylyl magnesium bromide. According to the NMR spectrum, the end product was 13-hydroxy-6-methoxy-2-(4-methoxyphenyl)-13-(2-phenoxyphenyl)-2-phenyl-indeno[2,1-f]naphtho[2,1-b]pyran.

This was cyclized analogously to step vii) in example 1 to spiro-9-xanthene-13'-[6-methoxy-2-(4-methoxyphenyl)-2-phenyl-indeno[2,1-f]naphtho[2,1-b]pyran] (0.4 g), which was identified by NMR spectroscopy.

Example 3

The procedure was analogous to example 1 with the exception that in step vi) the reaction was carried out with 2-benzylphenylmagnesium bromide (produced from 2-bromodiphenylmethane and magnesium in THF solution) instead of with 2-biphenylyl magnesium bromide. According to the NMR spectrum, 13-(2-benzylphenyl)-13-hydroxy-6-methoxy-2-(4-methoxyphenyl)-2-phenyl-indeno[2,1-f]naphtho[2,1-b]pyran was produced.

This was cyclized analogously to step vii) in example 1 to spiro-9-(9,10-dihydro anthracene)-13'-[6-methoxy-2-(4-methoxyphenyl)-2-phenyl-indeno[2,1-f]naphtho-[2,1-b]pyran] (0.5 g), which was identified by NMR spectroscopy.

Example 4

The procedure was carried out analogously to example 1, with the exception that in step i) the reaction was carried out with 3,4-dimethoxybenzylcyanide instead of with 3-methoxybenzylcyanide. After step vi), 13-(2-biphenylyl)-6,7-dimethoxy-13-hydroxy-2-(4-methoxyphenyl)-2-phenyl-indeno[2,-f]naphtho[2,1-b]pyran resulted and after cyclization analogous to step vii) in example 1, spiro-9-fluoreno-13'-[6,7-dimethoxy-2-(4-methoxyphenyl)-2-phenyl-indeno[2,1-f]naphtho[2,1-b]pyran] (0.6 g), which was identified by NMR spectroscopy.

Production of the test specimens:

500 ppm of the respective photochromic dye was dissolved in the monomer used (TRANSHADE-150 from the Tokuyama company; index of refraction 1.52) at room temperature with stirring. After addition of an initiator of the alkyl peroxyester type (1.5 weight-%), degassing was carried out twice and then polymerization was carried out according to the temperature program recommended by the Tokuyama company. The glass casting molds used in this process were dyed black so that all of the photochromic dyes could be incorporated in the matrix in unexcited state. After completion of the polymerization, the test specimens were tempered at 100° C. for 2 more hours.

Determination of the kinetic values and the longest wavelength absorption maxima:

To determine the bleaching rate, the test specimens produced in this way were measured in a kinetic test bench PTM II of the Zeiss company (irradiation with 50 klux according to DIN EN 1836, paragraph 6.1.3.1.1.). The illumination time was 15 minutes in each case, the bleaching time under dark conditions was 10 minutes. The temperature of the glass was regulated using a thermostatically controlled cuvette. During illumination and bleaching, the transmission—evaluated according to the light sensitivity of the human eye $V(\lambda)$—was respectively recorded at short time intervals. In addition to this, at the end of the illumination, the PTM II kinetic bank provides the UV/NIS spectrum of the darkened test specimen, from which the longest wavelength absorption maxima can be determined.

In the following Table 1 are listed the longest wave absorption maxima in darkened state and the half life time of the bleaching, i.e., the time from maximum darkening to a transmission that lies equidistant from the maximum darkening and bleaching of the spiro compounds according to the invention produced as described above as well as a prior art comparison compound, as described in U.S. Pat. No. 5,869,658, which has the following structural formula (III):

(III)

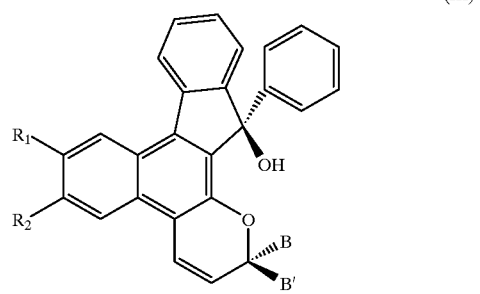

TABLE 1

| | $R_1$ | $R_2$ | B | B' | X | $\lambda_{max}$ | Bleaching half life |
|---|---|---|---|---|---|---|---|
| Example 1 | OMe | H | —$C_6H_4$OMe | H | — | 455 nm | 1 min |
| Example 2 | OMe | H | —$C_6H_4$OMe | H | O | 460 nm | 2 min |
| Example 3 | OMe | H | —$C_6H_4$OMe | H | $CH_2$ | 455 nm | 3 min |
| Example 4 | OMe | OMe | —$C_6H_4$OMe | H | — | 465 nm | 5 min |
| Comparison example from US-A 5,869,658 | OMe | OMe | —$C_6H_4$OMe | H | see formula (III) | 460 nm | 8 min |

Table 1 clearly shows the faster bleaching of the spiro compounds according to the invention in comparison to the prior art compound as described in U.S. Pat. No. 5,869,658.

What is claimed is:

1. A photochromic 3H-naphtho-[2,1-b]pyran compound corresponding to the formula (I):

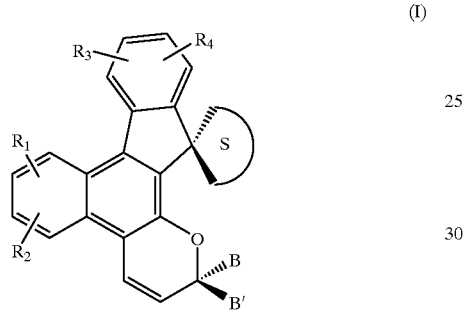

(I)

wherein $R_1$, $R_2$, $R_3$ and $R_4$ each independently represent a substituent selected from the group A, consisting of hydrogen, ($C_1$–$C_6$)-alkyl, ($C_1$–$C_6$)-alkoxy, ($C_3$–$C_7$)-cycloalkyl which may contain one or more heteroatoms, phenyl, hydroxy, bromine, chlorine and fluorine;

structural unit S together with the spiro carbon atom represents a saturated or unsaturated ring element with 5 to 8 carbon atoms, of which at most one can be replaced by a heteroatom selected from the group consisting of O, S and $NR_5$, wherein $R_5$ is straight-chain or branched ($C_1$–$C_6$)-alkyl, substituted or unsubstituted ($C_5$–$C_7$)-cycloalkyl, substituted or unsubstituted phenyl, or substituted or unsubstituted benzyl, wherein at least one aromatic or heteroaromatic ring system is anellated to said ring element, and said ring system is selected from the group E, consisting of benzene, naphthalene, phenanthrene, pyridine, quinoline, furan, thiophene, pyrrole, benzofuran, benzothiophene, indole and carbazole, and wherein said ring system may have one or more substituents selected from the group A;

B and B' are independently selected from the groups a), b), c) and d) wherein a) consists of monosubstituted, disubstituted and trisubstituted phenyl and naphthyl radicals;

b) consists of unsubstituted, monosubstituted and disubstituted heteroaryl radicals, wherein the heteroaryl radical is pyridyl, furanyl, benzofuran-2-yl, benzofuran-3-yl, thienyl, benzothien-2-yl or benzothien-3-yl;

wherein the substituents on the aryl or heteroaryl radicals in a) and b) are selected from the group consisting of hydroxy, amino, mono-($C_1$–$C_6$)-alkylamino, di-($C_1$–$C_6$)-alkylamino, monophenylamino and diphenylamino which are unsubstituted or monosubsituted on the phenyl rings, piperidinyl, morpholinyl, carbazolyl, unsubstituted, monosubstituted and disubstituted pyrryl, ($C_1$–$C_6$)-alkyl, ($C_1$–$C_6$)-alkoxy, bromine, chlorine and fluorine, wherein said aromatic and heteroaromatic ring systems can be substituted with ($C_1$–$C_6$)-alkyl, ($C_1$–$C_6$)-alkoxy, bromine, chlorine and fluorine;

c) consists of structural units corresponding to formula (V) or formula (W):

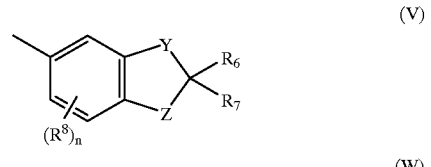

(V)

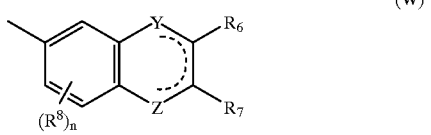

(W)

wherein

Y and Z are independently selected from the group consisting of O, S, CH, $CH_2$ and $NR_9$, wherein $R_9$ is selected from the group D, consisting of ($C_1$–$C_6$)-alkyl, ($C_1$–$C_6$)-acyl and hydrogen, $R_6$ and $R_7$ each independently represent hydrogen or ($C_1$–$C_6$)-alkyl, and $R_8$ is a substituent selected from the group A, wherein n is 1, 2 or 3, with the proviso that if Y in formula (V) is $NR_9$, Z is carbon, or d) B and B' together form an unsubstituted, monosubstituted or disubstituted fluorene-9-xylene radical or a saturated hydrocarbon radical that is $C_3$–$C_{12}$ spiromonocyclic, $C_7$–$C_{12}$ spirobicyclic or $C_7$–$C_{12}$ spirotricyclic, wherein the fluorene substituents are selected from group A.

2. A photochromic 3H-naphtho-[2,1-b]pyran according to claim 1, wherein the structural unit S in formula (I) together with the spiro carbon atom forms a substituted or unsubstituted fluorene, xanthene, thioxanthene or dihydroanthracene unit.

3. A photochromic 3H-naphtho-[2,1-b]pyran according to claim 1, corresponding to the formula (II):

(II)

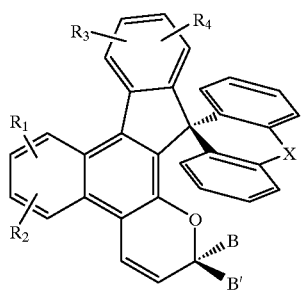

wherein

R₁, R₂, R₃ and R₄ are as defined above, and X represents —CH₂—, —O—, —S— or a C—C single bond between the phenyl rings.

4. A photochromic 3H-naphtho-[2,1-b]pyran according to claim 3, wherein B and B' are each independently selected from the group consisting of monosubstituted, disubstituted and trisubstituted aryl groups selected from phenyl and naphthyl.

5. A photochromic 3H-naphtho[2,1-b]pyran according to claim 1, selected from the group consisting of:

spiro-9-fluoreno-13'-[6-methoxy-2-(4-methoxyphenyl)-2-phenyl-indeno[2,1-f]naphtho[2,1-b]pyran];

spiro-9-xantheno-13'-[6-methoxy-2-(4-methoxyphenyl)-2-phenyl-indeno[2,1-f]naphtho[2,1-b]pyran];

spiro-9-thioxantheno-13'-[6-methoxy-2-(4-methoxyphenyl)-2-phenyl-indeno[2,1-f]naphtho[2,1-b]pyran];

spiro-9-(9,10-dihydroanthraceno)-13'-[6-methoxy-2-(4-methoxyphenyl)-2-phenyl-indeno[2,1-f]naphtho[2,1-b]pyran], and spiro-9-fluoreno-13'-[6,7-dimethoxy-2-(4-methoxyphenyl)-2-phenyl-indeno[2,1-f]naphtho[2,1-b]pyran].

6. A photochromic article comprising a body of synthetic resin material coated or impregnated with an effective photochromic amount of a photochromic ³H-naphtho[2,1-b]pyran compound according to claim 1.

7. A photochromic article according to claim 6, wherein said article is an ophthalmic lens.

* * * * *